United States Patent [19]

Cassal et al.

[11] Patent Number: 4,474,777

[45] Date of Patent: Oct. 2, 1984

[54] BENZODIAZEPINE DERIVATIVES AND THEIR PHARMACEUTICAL USE

[75] Inventors: Jean-Marie Cassal, Mulhouse, France; Albert E. Fischli; André Szente, both of Riehen, Switzerland

[73] Assignee: Hoffmann-La Roche Inc., Nutley, N.J.

[21] Appl. No.: 450,603

[22] Filed: Dec. 17, 1982

[30] Foreign Application Priority Data

Jan. 19, 1982 [CH] Switzerland .......................... 313/82

[51] Int. Cl.³ ..................... A61K 31/55; C07D 243/24
[52] U.S. Cl. ............................ 424/244; 260/239.3 D; 424/267; 424/274
[58] Field of Search ................ 260/239.3 D; 424/244, 424/267, 274

[56] References Cited

U.S. PATENT DOCUMENTS 4,299,767 11/1981 Fischli et al. ................ 260/239.3 D Primary Examiner—Robert T. Bond
Attorney, Agent, or Firm—Jon S. Saxe; Bernard S. Leon; Frank P. Hoffman

[57] ABSTRACT

There are presented novel pharmaceutically active substances which inhibit the intestinal resorption of cholesterol and which accordingly can be used in the control or prevention of atherosclerosis. These active substances are benzodiazepines of the formula

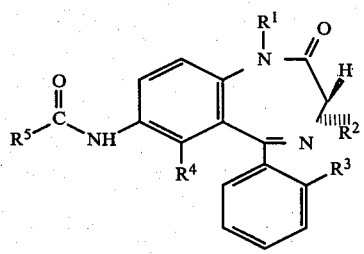

wherein $R^1$ is $(C_1-C_4)$-alkyl, $R^2$ is hydrogen or methyl, $R^3$ and $R^4$ each are halogen and $R^5$ is $(C_3-C_9)$-alkylamino substituted by at least two hydroxy groups, $(C_3-C_6)$-cycloalkylamino substituted by at least one hydroxy group, glucosamino, galactosamino, mannosamino, monohydroxy-1-azetidinyl, mono- or dihydroxy-1-pyrrolidinyl or mono-, di- or trihydroxy-1-piperidinyl, and the readily hydrolyzable esters and ethers thereof, as well as pharmaceutically acceptable salts of these compounds.

12 Claims, No Drawings

BENZODIAZEPINE DERIVATIVES AND THEIR PHARMACEUTICAL USE

DESCRIPTION OF THE INVENTION

The present invention relates to benzodiazepines. In particular, it is concerned with benzodiazepines of the formula

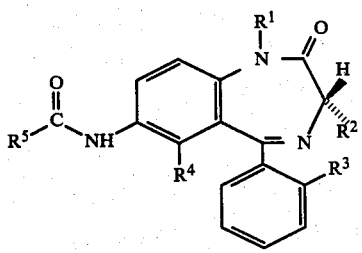

wherein $R^1$ is $(C_1-C_4)$-alkyl, $R^2$ is hydrogen or methyl, $R^3$ and $R^4$ each are halogen and $R^5$ is $(C_3-C_9)$-alkylamino substituted by at least two hydroxy groups, $(C_3-C_6)$-cycloalkylamino substituted by at least one hydroxy group, glucosamino, galactosamino, mannosamino, monohydroxy-1-azetidinyl, mono- or dihydroxy-1-pyrrolidinyl or mono-, di- or trihydroxy-1-piperidinyl, and the readily hydrolyzable esters and ethers thereof, as well as pharmaceutically acceptable salts of these compounds.

These products are novel; they are distinguished by valuable pharmacological properties and can be used in the control or prevention of illnesses.

Objects of the present invention are benzodiazepines of formula I above, their readily hydrolyzable esters and ethers, as well as pharmaceutically acceptable salts of these compounds per se and as pharmaceutically active substances, the manufacture of these products, medicaments containing such a product and the manufacture of such medicaments.

The term "$(C_1-C_4)$-alkyl" denotes straight-chain or branched-chain saturated hydrocarbon groups containing 1-4 carbon atoms such as methyl, ethyl, n-propyl, isopropyl, n-butyl and the like. The term "$(C_3-C_9)$-alkylamino substituted by at least two hydroxy groups" denotes straight-chain or branched-chain saturated hydrocarbon groups which on the one hand are linked via the group —NH— and on the other hand are substituted by at least two and at most four hydroxy groups, whereby the hydroxy groups can not be situated in the α-position to the group —NH—. Preferably, this term embraces groups containing 3-6 carbon atoms and two or three hydroxy groups such as 1,1-bis(hydroxymethyl)ethylamino, 2-hydroxy-1,1-bis(hydroxymethyl)ethylamino, 2-hydroxy-1-(hydroxymethyl)ethylamino, 2,3-dihydroxypropylamino and the like.

The term "$(C_3-C_6)$-cycloalkylamino substituted by at least one hydroxy group" denotes saturated cyclic hydrocarbon groups which on the one hand are linked via the group —NH— and on the other hand are substituted by at least one and at most three hydroxy groups, whereby the hydroxy group(s) can not be situated in the α-position to the group —NH—. The maximum number of hydroxy groups depends on the number of carbon atoms. 4-Hydroxycyclohexylamino is an example of such a substituted cycloalkylamino group.

Also, the hydroxy groups in the substituents monohydroxy-1-azetidinyl, mono- or dihydroxy-1-pyrrolidinyl or mono-, di- or trihydroxy-1piperidinyl can not be situated in the α-position to the nitrogen atom.

The term "halogen" signifies fluorine, chlorine, bromine or iodine.

The term "readily hydrolyzable esters and ethers thereof" signifies derivatives of benzodiazepines of formula I in which the hydroxy group(s) present in the group $R^5$ can be present wholly or partially in the form of a readily hydrolyzable ester and/or ether. Derivatives of benzodiazepines of formula I above which contain hydroxy groups modified in this manner are to some extent themselves pharmacologically active or represent biological precursors of pharmacologically active compounds. The term "readily hydrolyzable" is therefore intended to denote esters and ethers which are readily cleaved under physiological conditions. Readily hydrolyzable esters are, for example, esters or hemiesters with lower alkanecarboxylic acids or lower alkanedicarboxylic acids (e.g. acetates, formates, propionates, hemisuccinates and the like), cyclic diesters with lower alkanedicarboxylic acids (insofar as at least two free hydroxy groups are present), aromatic carboxylic acid esters (e.g. benzoates), araliphatic carboxylic acid esters (e.g. phehylacetates) and the like. Readily hydrolyzable ethers are, for example, open-chain or cyclic acetals or ketals, for example tetrahydropyranyl ethers, methoxymethyl ethers, 1,3-dioxolanes (insofar as at least two free hydroxy groups are present), lower alkyl ethers or the like. The following are examples of such modified groups $R^5$: 2-(acetyloxy)-1-[(acetyloxy)methyl]-1-methylethylamino, 2-(acetyloxy)-1-(hydroxymethyl)-1-methylethylamino, (2,2-dimethyl-1,3-dioxolan-4-yl)methylamino, 4-acetyloxy-1piperidinyl and the like. The present invention also includes other pharmaceutically acceptable biological precursors of benzodiazepines of formula I above which, after pharmaceutical administration, are converted under physiological conditions into the compounds of formula I above.

The term "lower" signifies that the thus-denoted compounds or groups contain up to 7 carbon atoms, preferably up to 4 carbon atoms, and can be straight-chain or branched-chain.

Among the products provided by the invention there are preferred those in which $R^1$ is methyl. $R^2$ preferably is methyl. $R^3$ preferably is chlorine. $R^4$ preferably is bromine. Benzodiazepines of formula I or pharmaceutically acceptable acid addition salts thereof are preferred and therein $R^5$ preferably is $(C_3-C_9)$-alkylamino substituted by at least two hydroxy groups.

A particularly preferred compound provided by the present invention is 1-[(S)-6-bromo-5-(o-chlorophenyl)-2,3-dihydro-1,3-dimethyl-2-oxo-1H-1,4-benzodiazepin-7-yl]-3-[1,1-bis(hydroxymethyl)ethyl]urea.

Other preferred compounds of formula I are:
1-[(S)-6-Bromo-5-(o-chlorophenyl)-2,3-dihydro-1,3-dimethyl-2-oxo-1H-1,4-benzodiazepin-7-yl]-3-[2-hydroxy-1,1-bis(hydroxymethyl)ethyl]urea,
1-[(S)-6-bromo-5-(o-chlorophenyl)-2,3-dihydro-1,3-dimethyl-2-oxo-1H-1,4-benzodiazepin-7-yl]-3-[2-hydroxy-1-(hydroxymethyl)ethyl]urea,
1-[(S)-6-bromo-5-(o-chlorophenyl)-2,3-dihydro-1,3-dimethyl-2-oxo-1H-1,4-benzodiazepin-7-yl]-3-(2,3-dihydroxypropyl)urea,
1-[(S)-6-bromo-5-(o-chlorophenyl)-2,3-dihydro-1,3-dimethyl-2-oxo-1H-1,4-benzodiazepin-7-yl]-3-(4-hydroxycyclohexyl)urea, N-[(S)-6-bromo-5-(o-chlorophenyl)-2,3-dihydro-1,3-dimethyl-2-oxo-1H-1,4-benzodiazepin-7-yl]-4-hydroxy-1-piperidinecarboxamide, N-[(S)-6-bromo-5-(o-chlorophenyl)-2,3-dihydro-1,3-dimethyl-2-oxo-1H-1,4-benzodiazepin-7-yl]-3-hydroxy-1-piperidinecarboxamide and 2-[3-[(S)-6-bromo-5-(o-chlorophenyl)-2,3-dihydro-1,3-dimethyl-2-oxo-1H-1,4-benzodiazepin-7-yl]ureido]-2-deoxy-D-glucose.

The benzodiazepines of formula I hereinbefore, their readily hydrolyzable esters and ethers, as well as the pharmaceutically acceptable salts of these compounds can be manufactured in accordance with the invention by (a) reacting a benzodiazepine of the formula

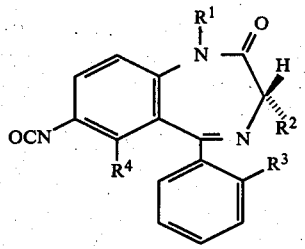

wherein $R^1$, $R^2$, $R^3$ and $R^4$ are as above,
with a compound of the formula $R^5$—H            III wherein $R^5$ is as above,
or with a derivative of a compound of formula III in which the hydroxy group(s) is/are present wholly or partially in the form of a readily hydrolyzable ester and/or ether, (b) if desired, hydrolyzing a resulting readily hydrolyzable ester or ether of a benzodiazepine of formula I, and/or (c) if desired, converting the free hydroxy group(s) in a resulting compound wholly or partially into readily hydrolyzable ester or ether groups, and/or (d) if desired, converting a resulting benzodiazepine of formula I or a readily hydrolyzable ester or ether thereof into a pharmaceutically acceptable salt.

For the manufacture of the products provided by the invention according to process variant (a), the benzodiazepine starting material of formula II is conveniently prepared shortly or immediately before the reaction with the amino compound of formula III or a readily hydrolyzable ester and/or ether thereof in the manner described below from a corresponding benzodiazepine of general formula IV and is introduced into the reaction as the crude product.

An amino compound of formula III or a readily hydrolyzable ester and/or ether thereof can then be added to a solution of the benzodiazepine of formula II in one of the inert organic solvents mentioned below. In this case, the amino compound can be used in the form of a solution or also in the absence of a solvent.

The reverse procedure can, however, be adopted, i.e. the solution containing the benzodiazepine of formula II can be added to the amino compound and, in this case, the amino compound is conveniently present in solution.

Suitable solvents for the benzodiazepine of formula II are, for example, halogenated hydrocarbons such as 1,2-dichloroethane, methylene chloride, chloroform, o-dichlorobenzene and the like, ethers such as tetrahydrofuran, dioxan, dimethoxyethane, diethylene glycol dimethyl ether and the like, acetone and the like. Suitable solvents for the amine of formula III or a readily hydrolyzable ester and/or ether thereof are the previously mentioned solvents, optionally mixtures thereof with water or water.

The reaction of a compound of formula II with an amino compound of formula III or a readily hydrolyzable ester and/or ether thereof is conveniently carried out at room temperature or at a temperature below room temperature.

In accordance with process variant (b), readily hydrolyzable esters and/or ethers of benzodiazepines of formula I can be hydrolyzed. The hydrolysis of corresponding esters is preferably carried out under mold alkaline conditions or enzymatically using an esterase, while corresponding ethers are preferably cleaved under mild acidic conditions. The hydrolysis is carried out in every respect according to methods known to a person skilled in the art. It must, however, be observed that of course there can be used only those methods which do not affect other structural elements present in the molecule.

In accordance with process variant (c), free hydroxy groups can be converted into readily hydrolyzable ester and/or ether groups. The manufacture of readily hydrolyzable esters and/or ethers is carried out in all respects according to methods which are known per se and which are familiar to any person skilled in the art. Readily hydrolyzable esters can be manufactured, for example, by reacting a corresponding hydroxy compound with a corresponding carboxylic acid chloride, a corresponding carboxylic acid anhydride or with another reactive carboxylic acid derivative. Suitable solvents are inert organic solvents such as halogenated hydrocarbons (e.g. methylene chloride, chloroform, 1,2-dichloroethane and the like), ethers (e.g. tetrahydrofuran, diethyl ether and the like), acetone dimethylformamide, dimethyl sulphoxide and the like.

Readily hydrolyzable ethers can be manufactured, for example, by reacting a corresponding hydroxy compound with a halide such as chlorodimethyl ether or the like in the presence of a base and in one of the inert organic solvents mentioned above, or by reacting a corresponding hydroxy compound in the presence of an acid with an enol ether such as 3,4-dihydropyran, or by reacting a corresponding hydroxy compound which contains at least two hydroxy groups in the presence of an acid with an aldehyde or a ketone such as acetone.

In accordance with process variant (d), the benzodiazepines of formula I above and their readily hydrolyzable esters and ethers can be converted into pharmaceutically acceptable salts. The manufacture of such pharmaceutically acceptable salts is carried out according to generally usual methods. As acid addition salts there come into consideration not only salts with pharmaceutically acceptable inorganic acids, but also salts with pharmaceutically acceptable organic acids; for example, hydrochlorides, hydrobromides, sulphates, citrates, acetates, succinates, methanesulphonates, p-toluenesulphonates and the like. If one of the hydroxy groups present in the group $R^5$ is in the form of a hemiester with a lower alkanedicarboxylic acid, then there also come into consideration salts with pharmaceutically acceptable bases; for example, sodium, potassium or calcium salts or salts with organic bases, for example with piperidine, diethylamine, N-methylglucamine, triethylamine, N-(2-aminoethyl)glycine or the like.

The benzodiazepines of formula II used as the starting materials can be prepared, as mentioned above, from corresponding benzodiazepines of the formula

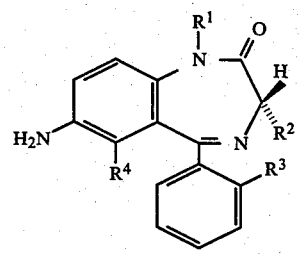

wherein $R^1$, $R^2$, $R^3$ and $R^4$ are as above,
namely by reaction with phosgene. This reaction is conveniently carried out by preparing a solution of phosgene in an organic solvent which is inert under the reaction conditions, then adding thereto while cooling a solution of a benzodiazepine of formula IV, thereupon heating the mixture to boiling under reflux for a time, again cooling and finally making the solution obtained basic or at least neutral with a tertiary organic amido compound such as triethylamine. The resulting solution, containing a benzodiazepine of formula II, can be stored for several hours with the exclusion of moisture and in the cold. By evaporation of the solution there is obtained the crude benzodiazepine of formula II which can be stored for several days with the exclusion of moisture and in the cold. Conveniently, the benzodiazepine of formula II is not purified, but is further processed in crude form.

The benzodiazepines of formula IV belong to a class of compound which is known per se and diverse specific representatives of this class of compound have already been described in the literature. Representatives of this class of compound which have still not been previously described specifically can be prepared according to methods which are known per se and which are familiar to any person skilled in the art. Detailed instructions concerning the preparation of benzodiazepines of formula IV are also given in the following Examples.

The benzodiazepines of formula I and to some extent also their readily hydrolyzable esters and ethers inhibit the intestinal resorption of cholesterol.

The inhibition of the intestinal resorption of cholesterol can be demonstrated in an experiment on animals as follows:

The substances to be investigated are administered to groups each comprising 6 normal female albino rats (body weight about 70 g) by means of a probang. Immediately thereafter the animals received by means of a probang a test feed containing a radioactive cholesterol. Thereafter, the faeces is collected for three days, freeze-dried and pulverized, and an aliquot is burnt in order to determine the radioactivity of the faeces. Untreated control animals excrete about 40–50% of the radioactive cholesterol taken up with the feed. The radioactive cholesterol which is not excreted is regarded as the resorbed cholesterol, the amount of resorbed cholesterol in the untreated control animals being arbitrarily fixed as 100%. Animals which have been treated with a substance inhibiting the intestinal resorption of cholesterol show a lower resorption of radioactive cholesterol than untreated control animals. The cholesterol resorption (CHORES) is expressed in percentages of the cholesterol resorption of untreated control animals.

In the following Table there are given the results obtained with representative products provided by the invention. There are given for each of the compounds listed therein the dosage administered (in μmol/kg p.o.) as well as the cholesterol resorption (CHORES) determined in percentages of the cholesterol resorption of untreated control animals. Moreover, the Table contains information concerning the acute toxicity of the compounds investigated ($LD_{50}$ in mg/kg in the case of single oral administration to mice).

TABLE

| Compound of formula I | | | | | Dosage in μmol/kg p.o. | CHORES in % | $LD_{50}$ in mg/kg p.o. |
|---|---|---|---|---|---|---|---|
| $R^1$ | $R^2$ | $R^3$ | $R^4$ | $R^5$ or modified $R^5$ | | | |
| $CH_3$ | $CH_3$ | Cl | Br | $-NHC(CH_3)(CH_2OH)_2$ | 100 | 31 | >5000 |
| $CH_3$ | $CH_3$ | Cl | Br | $-NHC(CH_2OH)_3$ | 100 | 30 | >5000 |
| $CH_3$ | $CH_3$ | Cl | Br | $-NHCH_2CH(OH)CH_2OH$ | 100 | 24 | — |
| $CH_3$ | $CH_3$ | Cl | Br | HO—⟨ ⟩—HN— | 100 | 34 | — |
| $CH_3$ | $CH_3$ | Cl | Br | —N⟨ ⟩OH | 100 | 44 | — |
| $CH_3$ | $CH_3$ | Cl | Br | —NHCH₂—⟨dioxolane⟩ | 100 | 25 | — |

The products provided by the invention can be used as medicaments, for example in the form of pharmaceutical preparations. The pharmaceutical preparations are administered orally (e.g. in the form of tablets, coated tablets, dragées, hard and soft gelatine capsules, solutions, emulsions or suspensions).

For the manufacture of pharmaceutical preparations the products provided by the invention can be processed with pharmaceutical inert inorganic or organic carriers. Examples of carriers which can be used for tablets, coated tablets, dragées and hard gelatine capsules are lactose, maize starch or derivatives thereof, talc, stearic acid or its salts and the like. Suitable carriers for soft gelatine capsules are, for example, vegetable oils, waxes, fats, semi-solid and liquid polyols and the like; depending on the nature of the active substance no carriers are, however, generally required in the case of soft gelatine capsules. Suitable carriers for the manufacture of solutions and syrups are, for example, water, polyols, saccharose, invert sugar, glucose and the like.

In addition, the pharmaceutical preparations can contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing a benzodiazepine of formula I, a readily hydrolyzable ester and/or ether or a pharmaceutically acceptable salt of such a compound are likewise an object of the present invention as is a process for the manufacture of such medicaments which comprises bringing one or more products provided by the invention and, if desired, one or more other therapeutically valuable substances into a galenical administration form. As mentioned earlier, the products provided by the invention can be used in the control or prevention of illnesses.

They can be used, in particular, in the control or prevention of atherosclerosis. The dosage can vary within wide limits and is, of course, fitted to the individual requirements in each particular case. In general, in the case of oral administration a daily dosage of about 50 mg to about 3 g, preferably from about 200 mg to about 1 g, should be appropriate.

The following Examples illustrate the present invention in more detail, but are not intended to limit its extent. All temperatures are given in degrees Centigrade.

EXAMPLE 1

(a) 53.6 g of carbobenzoxy-L-alanine are dissolved in 400 ml of dry tetrahydrofuran, the solution is treated dropwise with 30 g of thionyl chloride while cooling with ice and the mixture is stirred for 1 hour in the cold. A solution of 54 g (0.2 mol) of 2-amino-5-nitro-2'-chlorobenzophenone in 150 ml of dry tetrahydrofuran is subsequently added dropwise thereto rapidly, whereupon the mixture is stirred at room temperature for 24 hours. The solution obtained is concentrated, the residue is treated with ice and 10 percent sodium bicarbonate solution and extracted with methylene chloride. The organic solution is dried over sodium sulphate and evaporated. The residue is treated with dry ether, left to crystallize for 1 hour and then filtered while rinsing with ether/petroleum ether (1:1). After drying, there is obtained (S)-benzyl-[1-[[2-(o-chlorobenzoyl)-4-nitrophenyl]carbamoyl]ethyl]carbamate of melting point 143°–145°; $[\alpha]_{25}^D = 18°$ (1 percent solution in methylene chloride).

(b) 130 g (0.27 mol) of (S)-benzyl-[1-[[2-(o-chlorobenzoyl)-4-nitrophenyl]carbamoyl]ethyl]carbamate are dissolved in 350 ml of a 30 to 33 percent solution of hydrogen bromide in glacial acetic acid, the solution is stirred at room temperature for 30 minutes, evaporated, treated with water and extracted three times with ether. The aqueous solution is cooled in ice, neutralized with solid sodium bicarbonate and extracted with methylene chloride. The organic phase is dried over sodium sulphate and evaporated. The residue is treated with 80 ml of glacial acetic acid and 800 ml of toluene, the mixture is heated to boiling under reflux for 20 minutes and then evaporated. The residual oil is taken up in methylene chloride, washed with saturated sodium bicarbonate solution, dried over sodium sulphate and evaporated. The residue is dissolved in 500 ml of benzene, the solution is seeded with racemic 5-(o-chlorophenyl)-1,3-dihydro-3-methyl-7-nitro-2H-1,4-benzodiazepin-2-one and left to stand at room temperature overnight. The crystalline material is filtered off and the mother liquor is evaporated. After recrystallization of the residue from ether, there is obtained (S)-5-(o-chlorophenyl)-1,3-dihydro-3-methyl-7-nitro-2H-1,4-benzodiazepin-2-one of melting point 200°–202°; $[\alpha]_{25}^D = +241°$ (1 percent solution in methylene chloride).

(c) 100 g (0.3 mol) of (S)-5-(o-chlorophenyl)-1,3-dihydro-3-methyl-7-nitro-2H-1,4-benzodiazepin-2-one are dissolved in 700 ml of dry acetone. The solution is treated with 79 ml of ground potassium carbonate and with 31.4 ml of methyl iodide and the mixture is stirred at room temperature for 4 hours. The mixture is treated with 30 ml of glacial acetic acid and evaporated. The residue is treated with an ice/water mixture and extracted several times with methylene chloride. The organic phase is washed with water, dried over sodium sulphate, concentrated and treated with methanol. After filtering off the separated crystals, there is obtained (S)-5-(o-chlorophenyl)-1,3-dihydro-1,3-dimethyl-7-nitro-2H-1,4-benzodiazepin-2-one of melting point 159°; $[\alpha]_{25}^D = +381.2°$ (1 percent solution in methylene chloride).

(d) A solution of 68.2 g (0.198 mol) of (S)-5-(o-chlorophenyl)-1,3-dihydro-1,3-dimethyl-7-nitro-2H-1,4-benzodiazepin-2-one in a mixture of 400 ml of tetrahydrofuran and 950 ml of methanol is treated with Raney-nickel which has previously been washed several times with methanol and tetrahydrofuran and the suspension is hydrogenated while stirring and cooling with water, whereupon it is filtered and the filtrate is evaporated. The residue is recrystallized from ether, there being obtained (S)-7-amino-5-(o-chlorophenyl)-1,3-dihydro-1,3-dimethyl-2H-1,4-benzodiazepin-2-one of melting point 221°; $[\alpha]_{25}^D = -13.8°$ (1 percent solution in methylene chloride).

(e) A solution of 75 g (0.239 mol) of (S)-7-amino-5-(o-chlorophenyl)-1,3-dihydro-1,3-dimethyl-2H-1,4-benzodiazepin-2-one in 1500 ml of glacial acetic acid is cooled to 0°, treated rapidly with a solution of 12.5 ml of bromine in 350 ml of glacial acetic acid and then the mixture is stirred at 0° for a further 30 minutes. The mixture is treated with ice/water and extracted with methylene chloride. The organic extract is dried over sodium sulphate and evaporated. The residue obtained is recrystallized from methylene chloride/ether and there is obtained (S)-7-amino-6-bromo-5-(o-chlorophenyl)-1,3-dihydro-1,3-dimethyl-2H-1,4-benzodiazepin-2-one of melting point 243°; $[\alpha]_{25}^D = 41.7°$ (1 percent solution in methylene chloride).

(f) 50 g (0.127 mol) of (S)-7-amino-6-bromo-5-(o-chlorophenyl)-1,3-dihydro-1,3-dimethyl-2H-1,4-benzodiazepin-2-one are dissolved in 700 ml of 1,2-dichloroethane while warming and the still hot solution is added dropwise while stirring and cooling to a mixture of 90 ml (0.173 mol) of a 20 percent solution of phosgene in toluene and 500 ml of dichloroethane in such a manner that the temperature does not exceed 10°. The mixture is subsequently heated to boiling under reflux while stirring for 1 hour, 500 ml of 1,2-dichloroethane are distilled off, the solution is cooled to 10°, made basic with triethylamine and evaporated, there being obtained (S)-[6-bromo-5-(o-chlorophenyl)-2,3-dihydro-1,3-dimethyl-2-oxo-1H-1,4-benzodiazepin-7-yl]isocyanate as a foam which can be stored for several days in a refrigerator with the exclusion of moisture.

(g) A solution of (S)-[6-bromo-5-(o-chlorophenyl)-2,3-dihydro-1,3-dimethyl-2-oxo-1H-1,4-benzodiazepin-7-yl]isocyanate [obtained in accordance with the details in paragraph (f) above from 5 g (0.0127 mol) of (S)-7-amino-6-bromo-5-(o-chlorophenyl)-1,3-dihydro-1,3-dimethyl-2H-1,4-benzodiazepin-2-one] in 1,2-dichloroethane is treated with a dichloroethane solution of 1.3 g of 4-hydroxypiperidine, the mixture is stirred at room temperature for 1 hour and then evaporated. The residue is taken up in methylene chloride, washed with water, dried over sodium sulphate and evaporated. By chromatography on silica gel while eluting with ethyl acetate and recrystallization from ether there is obtained N-[(S)-6-bromo-5-(o-chlorophenyl)-2,3-dihydro-1,3-dimethyl-2-oxo-1H-1,4-benzodiazepin-7-yl]-4-hydroxy-1-piperidinecarboxamide of melting point 140° (decomposition); $[\alpha]_{25}^D = +31.6°$ (1 percent solution in methylene chloride.

EXAMPLE 2

A solution of (S)-[6-bromo-5-(o-chlorophenyl)-2,3-dihydro-1,3-dimethyl-2-oxo-1H-1,4-benzodiazepin-7-yl]isocyanate [obtained in accordance with the details in Example 1(f) from 2.81 g (0.0072 mol) of (S)-7-amino-6-bromo-5-(o-chlorophenyl)-1,3-dihydro-1,3-dimethyl-2H-1,4-benzodiazepin-2-one] in acetone is treated with a solution of 1.3 g (0.0107 mol) of tris(hydroxymethyl)amino-methane in 5 ml of water, whereupon the mixture is stirred at room temperature for 15 minutes and extracted with ethyl acetate. The organic extract is dried over sodium sulphate and evaporated. The residue is recrystallized from tetrahydrofuran/1,2-dichloroethane and yields 1-[(S)-6-bromo-5-(o-chlorophenyl)-2,3-dihydro-1,3-dimethyl-2-oxo-1H-1,4-benzodiazepin-7-yl]-3-[2-hydroxy-1,1-bis(hydroxymethyl)ethyl]urea of melting point 175° (decomposition); $[\alpha]_{25}^D = +22.87°$ (0.8 percent solution in methanol).

EXAMPLE 3

A solution of (S)-[6-bromo-5-(o-chlorophenyl)-2,3-dihydro-1,3-dimethyl-2-oxo-1H-1,4-benzodiazepin-7-yl]isocyanate [obtained in accordance with the details in Example 1(f) from 5 g (0.0127 mol) of (S)-7-amino-6-bromo-5-(o-chlorophenyl)-1,3-dihydro-1,3-dimethyl-2H-1,4-benzodiazepin-2-one] in tetrahydrofuran is treated with a solution of 5 g (0.039 mol) of 2-amino-1,3-propanediol hydrochloride and 4 g (0.04 mol) of potassium bicarbonate in 20 ml of water. The mixture is stirred at room temperature for 30 minutes, whereupon the tetrahydrofuran is removed by evaporation and the residue is extracted several times with ethyl acetate. The organic phase is dried over sodium sulphate and evaporated, whereupon the residue is recrystallized from methylene chloride. There is obtained 1-[(S)-6-bromo-5-(o-chlorophenyl)-2,3-dihydro-1,3-dimethyl-2-oxo-1H-1,4-benzodiazepin-7-yl]-3-[2-hydroxy-1-(hydroxymethyl)ethyl]urea of melting point 184° (decomposition); $[\alpha]_{25}^D = +23.63°$ (0.8 percent solution in methanol).

EXAMPLE 4

A solution of (S)-[6-bromo-5-(o-chlorophenyl)-2,3-dihydro-1,3-dimethyl-2-oxo-1H-1,4-benzodiazepin-7-yl]isocyanate [obtained in accordance with the details in Example 1(f) from 5 g (0.0127 mol) of (S)-7-amino-6-bromo-5-(o-chlorophenyl)-1,3-dihydro-1,3-dimethyl-2H-1,4-benzodiazepin-2-one] in tetrahydrofuran is treated with a solution of 4.4 g (0.043 mol) of 3-amino-1,2-propanediol in 50 ml of tetrahydrofuran and 10 ml of water. The mixture is stirred at room temperature for 1 hour and extracted with methylene chloride, whereupon the organic extract is dried over sodium sulphate and evaporated. The residue is chromatographed on silica gel while eluting with ethyl acetate/methanol (95:5) and then recrystallized from ether. There is obtained 1-[(S)-6-bromo-5-(o-chlorophenyl)-2,3-dihydro-1,3-dimethyl-2-oxo-1H-1,4-benzodiazepin-7-yl]-3-(2,3-dihydroxypropyl)urea of melting point 175°; $[\alpha]_{25}^D = +57.5°$ (0.8 percent solution in dioxan).

EXAMPLE 5

A solution of (S)-[6-bromo-5-(o-chlorophenyl)-2,3-dihydro-1,3-dimethyl-2-oxo-1H-1,4-benzodiazepin-7-yl]isocyanate [obtained in accordance with the details in Example 1(f) from 2.8 g (0.0072 mol) of (S)-7-amino-6-bromo-5-(o-chlorophenyl)-1,3-dihydro-1,3-dimethyl-2H-1,4-benzodiazepin-2-one] in acetone is treated with a solution of 2.4 ml of 4-aminocyclohexanol in 10 ml of acetone, the mixture is stirred at room temperature for 15 minutes, treated with water and extracted with ethyl acetate. The ethyl acetate solution is dried over sodium sulphate and evaporated, whereupon the residue is chromatographed on silica gel while eluting with chloroform and ethyl acetate and recrystallized from methylene chloride. There is obtained 1-[(S)-6-bromo-5-(o-chlorophenyl)-2,3-dihydro-1,3-dimethyl-2-oxo-1H-1,4-benzodiazepin-7-yl]-3-(4-hydroxycyclohexyl)urea of melting point 226°–227°; $[\alpha]_{25}^D = +22.63°$ (0.8 percent solution in methanol).

EXAMPLE 6

A solution of (S)-[6-bromo-5-(o-chlorophenyl)-2,3-dihydro-1,3-dimethyl-2-oxo-1H-1,4-benzodiazepin-7-yl]isocyanate [obtained in accordance with the details in Example 1(f) from 15 g (0.038 mol) of (S)-7-amino-6-bromo-5-(o-chlorophenyl-1,3-dihydro-1,3-dimethyl-2H-1,4-benzodiazepin-2-one] in acetone is treated with 4.02 g (0.038 mol) of 2-amino-2-methyl-1,3-propanediol, the mixture is stirred at room temperature for 1 hour and then evaporated. The residue is chromatographed on silica gel while eluting with ethyl acetate. After recrystallization from acetone/hexane, there is obtained 1-[(S)-6-bromo-5-(o-chlorophenyl)-2,3-dihydro-1,3-dimethyl-2-oxo-1H-1,4-benzodiazepin-7-yl]-3-[1,1-bis(hydroxymethyl)ethyl]urea of melting point 190° (decomposition); $[\alpha]_{25}^D = +25.2°$ (0.8 percent solution in methanol).

EXAMPLE 7

In analogy to the details in Example 1(g), but using 3-hydroxypiperidine in place of 4-hydroxypiperidine, there is obtained N-[(S)-6-bromo-5-(o-chlorophenyl)-2,3-dihydro-1,3-dimethyl-2-oxo-1H-1,4-benzodiazepin-7-yl]-3-hydroxy-1-piperidinecarboxamide of melting point 140° (decomposition); $[\alpha]_{25}^D = +30.8°$ (1 percent solution in methylene chloride).

EXAMPLE 8

A solution of (S)-[6-bromo-5-(o-chlorophenyl)-2,3-dihydro-1,3-dimethyl-2-oxo-1H-1,4-benzodiazepin-7-yl]isocyanate [obtained in accordance with details in Example 1(f) from 10 g (0.0254 mol) of (S)-7-amino-6-bromo-5-(o-chlorophenyl)-1,3-dihydro-1,3-dimethyl-2H-1,4-benzodiazepin-2-one] in acetone is treated with a solution of 16 g of D-glucosamine hydrochloride and 7.3 g of potassium carbonate in 100 ml of water, the mixture is stirred at room temperature for 10 minutes and extracted several times with ethyl acetate. The organic phase is dried over sodium sulphate and evaporated, whereupon the residue is recrystallized from tetrahydrofuran/methylene chloride. There is obtained 2-[3-[(S)-6-bromo-5-(o-chlorophenyl)-2,3-dihydro-1,3-dimethyl-2-oxo-1H-1,4-benzodiazepin-7-yl]ureido]-2-deoxy-D-glucose as a diastereomeric mixture with a melting point of 185° (decomposition); $[\alpha]_{25}^D = +45°$ (0.8 percent solution in methanol).

EXAMPLE 9

A solution of (S)-[6-bromo-5-(o-chlorophenyl)-2,3-dihydro-1,3-dimethyl-2-oxo-1H-1,4-benzodiazepin-7-yl]isocyanate [obtained in accordance with details in Example 1(f) from 4 g (0.01 mol) of (S)-7-amino-6-bromo-5-(o-chlorophenyl)-1,3-dihydro-1,3-dimethyl-2H-1,4-benzodiazepin-2-one] in acetone is treated with a solution of 3.8 g (0.04 mol) of 3-amino-1,2-propanediol in 10 ml of water and 50 ml of acetone, the mixture is stirred at room temperature for 12 hours and extracted with methylene chloride. The organic extract is dried over sodium sulphate and evaporated, whereupon the residue is chromatographed on silica gel while eluting with chloroform. There is obtained 1-[(S)-6-bromo-5-(o-chlorophenyl)-2,3-dihydro-1,3-dimethyl-2-oxo-1H-1,4-benzodiazepin-7-yl]-3-[(2,2-dimethyl-1,3-dioxolan-4-yl)methyl]urea of melting point 135° (decomposition); $[\alpha]_{25}^D = +7.6°$ (0.8 percent solution in methanol).

EXAMPLE 10

A solution of 5 g of 1-[(S)-6-bromo-5-(o-chlorophenyl)-2,3-dihydro-1,3-dimethyl-2-oxo-1H-1,4-benzodiazepin-7-yl]-3-[1,1-bis(hydroxymethyl)ethyl]urea in pyridine is treated with 4 ml of acetic anhydride, the mixture is stirred at room temperature for 1 hour, treated with water and extracted with methylene chloride. The organic phase is dried over sodium sulphate and evaporated, whereupon the residue is chromatographed on silica gel while eluting with chloroform and then recrystallized from petroleum ether. There is obtained (S)-N-[2-(acetyloxy)-1-[(acetyloxy)methyl]-1-methylethyl]-N'-[6-bromo-5-(o-chlorophenyl)-2,3-dihydro-1,3-dimethyl-2-oxo-1H-1,4-benzodiazepin-7-yl]urea of melting point 105°-107° (decomposition); $[\alpha]_{25}^D = +33.75°$ (0.8 percent solution in methylene chloride).

EXAMPLE 11

(a) A solution of (S)-[6-bromo-5-(o-chlorophenyl)-2,3-dihydro-1,3-dimethyl-2-oxo-1H-1,4-benzodiazepin-7-yl]isocyanate [obtained in accordance with the details in Example 1(f) from 4 g (0.01 mol) of (S)-7-amino-6-bromo-5-(o-chlorophenyl)-1,3-dihydro-1,3-dimethyl-2H-1,4-benzodiazepin-2-one] in acetone is treated with a solution of 1.44 g (0.011 mol) of 2,2-dimethyl-1,3-dioxolan-4-methylamine in acetone and the mixture is stirred at room temperature for 12 hours. The acetone is removed by evaporation, whereupon the residue is chromatographed on silica gel while eluting with chloroform. There is obtained 1-[(S)-6-bromo-5-(o-chlorophenyl)-2,3-dihydro-1,3-dimethyl-2-oxo-1H-1,4-benzodiazepin-7-yl]-3-[(2,2-dimethyl-1,3-dioxolan-4-yl)methyl]urea of melting point 135° (decomposition).

(b) A solution of 1-[(S)-6-bromo-5-(o-chlorophenyl)-2,3-dihydro-1,3-dimethyl-2-oxo-1H-1,4-benzodiazepin-7-yl]-3-[(2,2-dimethyl-1,3-dioxolan-4-yl)methyl]urea in ethanol is stirred at room temperature for 5 hours with 1N hydrochloric acid. The mixture is extracted with ethyl acetate, washed with water, dried over sodium sulphate and evaporated. The residue is chromatographed on silica gel while eluting with ethyl acetate/methanol (95:5). After recrystallization from methanol/ether, there is obtained 1-[(S)-6-bromo-5-(o-chlorophenyl)-2,3-dihydro-1,3-dimethyl-2-oxo-1H-1,4-benzodiazepin-7-yl]-3-(2,3-dihydroxypropyl)urea of melting point 175° (decomposition).

EXAMPLE A

1-[(S)-6-Bromo-5-(o-chlorophenyl)-2,3-dihydro-1,3-dimethyl-2-oxo-1H-1,4-benzodiazepin-7-yl]-3-[1,1-bis(hydroxymethyl)ethyl]urea can be used as follows as the active substance for the manufacture of pharmaceutical preparations:

| (a) Tablets | 1 tablet contains |
| --- | --- |
| Active substance | 200 mg |
| Microcrystalline cellulose | 155 mg |
| Maize starch | 25 mg |
| Talc | 25 mg |
| Hydroxypropylmethylcellulose | 20 mg |
| | 425 mg |

The active substance is mixed with half of the microcrystalline cellulose and the mixture is granulated with a 10 percent solution of hydroxypropylmethylcellulose in a mixture of isopropanol and methylene chloride. The granulate is dried, sieved and mixed with the remainder of the adjuvants. Then, the mixture is pressed on a press to biplanar tablets having a diameter of 12 mm and a break-bar.

| (b) Capsules | 1 capsule contains |
| --- | --- |
| Active substance | 100.0 mg |
| Maize starch | 20.0 mg |
| Lactose | 95.0 mg |
| Talc | 4.5 mg |
| Magnesium stearate | 0.5 mg |
| | 220.0 mg |

The active substance is mixed with the adjuvants and the mixture is sieved. After renewed mixing, the capsule fill mass obtained is filled into interlocking gelatine capsules of suitable size on a fully automatic capsule filling machine.

What is claimed:
1. A compound of the formula

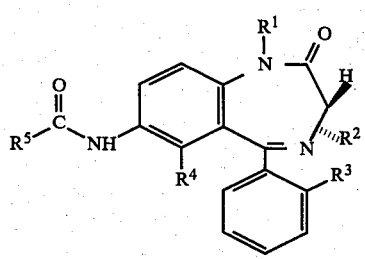

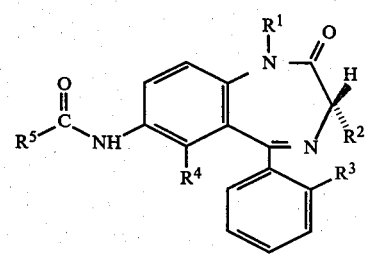

wherein $R^1$ is $(C_1-C_4)$-alkyl, $R^2$ is hydrogen or methyl, $R^3$ and $R^4$ each are halogen and $R^5$ is $(C_3-C_9)$-alkylamino substituted by two to four hydroxy groups, $(C_3-C_6)$-cycloalkylamino substituted by one to three hydroxy groups, glucosamino, galactosamino, mannosamino, monohydroxy-1-azetidinyl, mono- or dihydroxy-1-pyrrolidinyl or mono-, di- or trihydroxy-1-piperidinyl,
and the readily hydrolyzable esters selected from the group consisting of esters of hemiesters of lower alkanecarboxylic acids or lower alkanedicarboxylic acids, cyclic diesters of lower alkanedicarboxylic acids, aromatic carboxylic acid esters and araliphatic carboxylic acid esters and ethers selected from the group consisting of open chain or cyclic ketals or acetals and lower alkyl ethers thereof, as well as pharmaceutically acceptable salts of these compounds.

2. The compound of claim 1 wherein $R^1$ is methyl.
3. The compound of claim 2 wherein $R^2$ is methyl.
4. The compound of claim 3 wherein $R^3$ is chlorine.
5. The compound of claim 4 wherein $R^4$ is bromine.
6. The compound of claim 5 wherein $R^5$ is $(C_3-C_9)$-alkylamino substituted by at least two hydroxy groups.
7. The compound: 1-[(S)-6-Bromo-5-(o-chlorophenyl)-2,3-dihydro-1,3-dimethyl-2-oxo-1H-1,4-benzodiazepin-7-yl]-3-[1,1-bis(hydroxymethyl)ethyl]urea.
8. A compound selected from the group consisting of 1-[(S)-6-Bromo-5-(o-chlorophenyl)-2,3-dihydro-1,3-dimethyl-2-oxo-1H-1,4-benzodiazepin-7-yl]-3-(2,2-dimethyl-1,3-dioxolan-4-yl)methyl]urea or (S)-N-[2-(acetyloxy)-1-[(acetyloxy)methyl]-1-methylethyl]-N'-[6-bromo-5-(o-chlorophenyl)-2,3-dihydro-1,3-dimethyl-2-oxo-1H-1,4-benzodiazepin-7-yl]urea.
9. A compound selected from the group consisting of 1-[(S)-6-Bromo-5-(o-chlorophenyl)-2,3-dihydro-1,3-dimethyl-2-oxo-1H-1,4-benzodiazepin-7-yl]-3-[2-hydroxy-1,1-bis(hydroxymethyl)ethyl]urea, 1-[(S)-6-bromo-5-(o-chlorophenyl)-2,3-dihydro-1,3-dimethyl-2-oxo-1H-1,4-benzodiazepin-7-yl]-3-[2-hydroxy-1-(hydroxymethyl)ethyl]urea, 1-[(S)-6-bromo-5-(o-chlorophenyl)-2,3-dihydro-1,3-dimethyl-2-oxo-1H-1,4-benzodiazepin-7-yl]-3-(2,3-dihydroxypropyl)urea, 1-[(S)-6-bromo-5-(o-chlorophenyl)-2,3-dihydro-1,3-dimethyl-2-oxo-1H-1,4-benzodiazepin-7-yl]-3-(4-hydroxycyclohexyl)urea, N-[(S)-6-bromo-5-(o-chlorophenyl)-2,3-dihydro-1,3-dimethyl-2-oxo-1H-1,4-benzodiazepin-7-yl]-4-hydroxy-1-piperidinecarboxamide, N-[(S)-6-bromo-5-(o-chlorophenyl)-2,3-dihydro-1,3-dimethyl-2-oxo-1H-1,4-benzodiazepin-7-yl]-3-hydroxy-1-piperidinecarboxamide or 2-[3-[(S)-6-bromo-5-(o-chlorophenyl)-2,3-dihydro-1,3-dimethyl-2-oxo-1H-1,4-benzodiazepin-7-yl]ureido]-2-deoxy-D-glucose.
10. A process for the manufacture of a compound of the formula wherein $R^1$ is $(C_1-C_4)$-alkyl, $R^2$ is hydrogen or methyl, $R^3$ and $R^4$ each are halogen and $R^5$ is $(C_3-C_9)$-alkylamino substituted by two to four hydroxy groups, $(C_3-C_6)$-cycloalkylamino substituted by one to three hydroxy groups, glucosamino, galactosamino, mannosamino, monohydroxy-1-azetidinyl, mono- or dihydroxy-1-pyrrolidinyl or mono-, di- or trihydroxy-1-piperidinyl,
and the readily hydrolyzable esters selected from the group consisting of esters or hemiesters of lower alkanecarboxylic acids or lower alkanedicarboxylic acids, cyclic diesters of lower alkanedicarboxylic acids, aromatic carboxylic acid esters and araliphatic carboxylic acid esters and ethers selected from the group consisting of open chain or cyclic ketals or acetals and lower alkyl ethers thereof, as well as pharmaceutically acceptable salts of these compounds which comprises
(a) reacting a compound of the formula

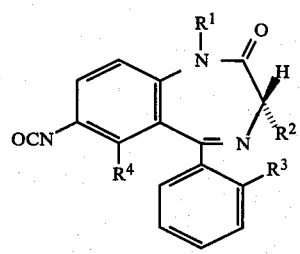

wherein $R^1$, $R^2$, $R^3$ and $R^4$ are as above,
with a compound of the formula $R^5$—H           III wherein $R^5$ is as above,
or with a derivative of a compound of formula III in which they hydroxy group(s) is/are wholly or partially present in the form of a readily hydrolyzable ester and-/or ether as above and/or
(b) if desired, hydrolyzing a resulting readily hydrolyzable ester or ether of the above benzodiazepine of formula I,
(c) if desired, converting the free hydroxy group(s) in a resulting compound wholly or partially into a readily hydrolyzable ester and/or ether as above, and/or
(d) if desired, converting a resulting benzodiazepine of formula I or a readily hydrolyzable ester or ether above into a pharmaceutically acceptable salt.
11. A method of treating atherosclerosis in a patient in need of such treatment which comprises administering to said patient a therapeutically effective dose of a compound of claim 1.
12. A method of treating atherosclerosis in a patient in need of such treatment which comprises administering to said patient a therapeutically effective dose of 1-[(S)-6-bromo-5-(o-chlorophenyl)-2,3-dihydro-1,3-dimethyl-2-oxo-1H-1,4-benzodiazepin-7-yl]-3-[1,1-bis(hydroxymethyl)ethyl]urea.

* * * * *